(12) United States Patent
Song et al.

(10) Patent No.: US 8,263,084 B2
(45) Date of Patent: Sep. 11, 2012

(54) PHARMACEUTICAL COMPOSITION FOR TREATING OBESITY-RELATED DISEASE COMPRISING INSULINOTROPIC PEPTIDE CONJUGATE

(75) Inventors: Dae Hae Song, Seoul (KR); Min Young Kim, Suwon-si (KR); Young Jin Park, Suwon-si (KR); Eun Hee Kang, Yangsan-si (KR); Sung Youb Jung, Suwon-si (KR); Se Chang Kwon, Seoul (KR); Gwan Sun Lee, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

(21) Appl. No.: 12/744,660

(22) PCT Filed: Nov. 28, 2008

(86) PCT No.: PCT/KR2008/007074
§ 371 (c)(1),
(2), (4) Date: Sep. 8, 2010

(87) PCT Pub. No.: WO2009/069983
PCT Pub. Date: Jun. 4, 2009

(65) Prior Publication Data
US 2010/0330108 A1    Dec. 30, 2010

(30) Foreign Application Priority Data
Aug. 26, 2008 (KR) .................. 10-2008-0083194

(51) Int. Cl.
*A61K 39/395* (2006.01)
*A61P 5/50* (2006.01)
(52) U.S. Cl. .................................. 424/195.11; 514/6.7
(58) Field of Classification Search .................. None
See application file for complete search history.

(56) References Cited

U.S. PATENT DOCUMENTS

| | | | |
|---|---|---|---|
| 6,528,486 B1 * | 3/2003 | Larsen et al. | 514/6.8 |
| 6,956,026 B2 | 10/2005 | Beeley et al. | |
| 6,989,366 B2 | 1/2006 | Beeley et al. | |
| 7,105,490 B2 | 9/2006 | Beeley et al. | |
| 7,115,569 B2 | 10/2006 | Beeley et al. | |
| 7,271,149 B2 * | 9/2007 | Glaesner et al. | 514/7.2 |
| 2003/0195154 A1 * | 10/2003 | Walker et al. | 514/12 |
| 2006/0275254 A1 | 12/2006 | Kim et al. | |
| 2007/0041967 A1 | 2/2007 | Jung et al. | |
| 2008/0119390 A1 | 5/2008 | Mozes | |
| 2009/0053246 A1 | 2/2009 | Kim et al. | |

FOREIGN PATENT DOCUMENTS

| | | |
|---|---|---|
| KR | 10-2005-0047031 A | 5/2005 |
| KR | 10-2006-0106486 A | 10/2006 |
| WO | 97/46584 A1 | 12/1997 |
| WO | 99/07404 A1 | 2/1999 |
| WO | WO 2006/107124 A1 | 10/2006 |
| WO | 2007/049940 A1 | 5/2007 |
| WO | WO 2007/112069 A2 | 10/2007 |
| WO | 2008/082274 A1 | 7/2008 |

OTHER PUBLICATIONS

Meeran et al. Repeated Intracerebroventricular Administration of Glucagon-Like Peptide-1-(7-36) Amide or Exendin (9-39) Alters Body Weight in the Rat, Endocrinology 140:244-250 (1999) The Endocrine Society, U.S.A.

New Zealand Patent Office, New Zealand Office Action issued in corresponding NZ Application No. 585314, dated Feb. 18, 2011.

Qinghua Wang, "Novel GLP-1 Fusion Peptides as Potential Therapies for the Prevention and Treatment of Diabetes," Endocrinology Rounds, 2007, vol. 7, issue 3, pp. 1-6.

Russian Patent Office, Russian Office Action issued in corresponding RU Application No. 2010126478/15, dated Nov. 8, 2011.

* cited by examiner

*Primary Examiner* — Gyan Chandra
(74) *Attorney, Agent, or Firm* — Sughrue Mion, PLLC

(57) ABSTRACT

The present invention relates to a composition for treating obesity-related diseases comprising an insulinotropic peptide conjugate, more particularly, to a composition for treating obesity-related diseases comprising a conjugate prepared by covalently linking the insulinotropic peptide with a carrier substance via a non-peptidyl linker, and a method for treating obesity-related diseases by using the same. In particular, the composition for treating obesity-related diseases according to the present invention remarkably improves the efficacy of suppressing food intake and its duration to reduce body weight and body fat, thereby being useful for the treatment of obesity-related diseases.

6 Claims, 5 Drawing Sheets

[Fig. 1]
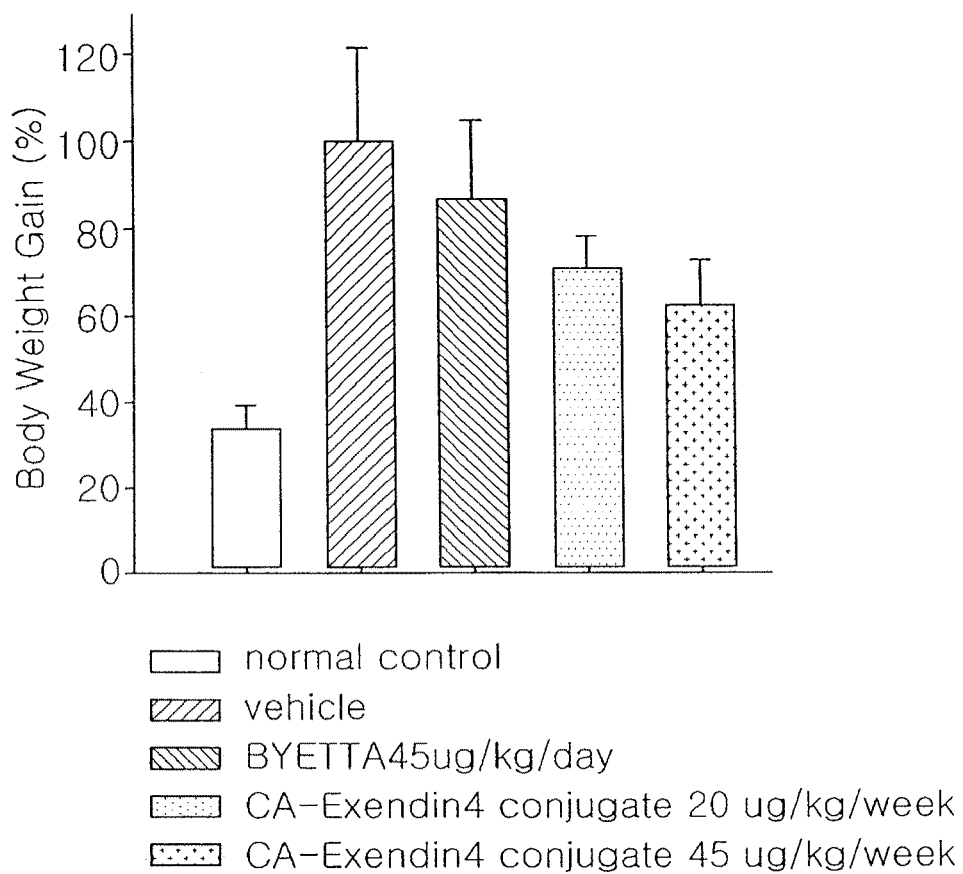

[Fig. 2]
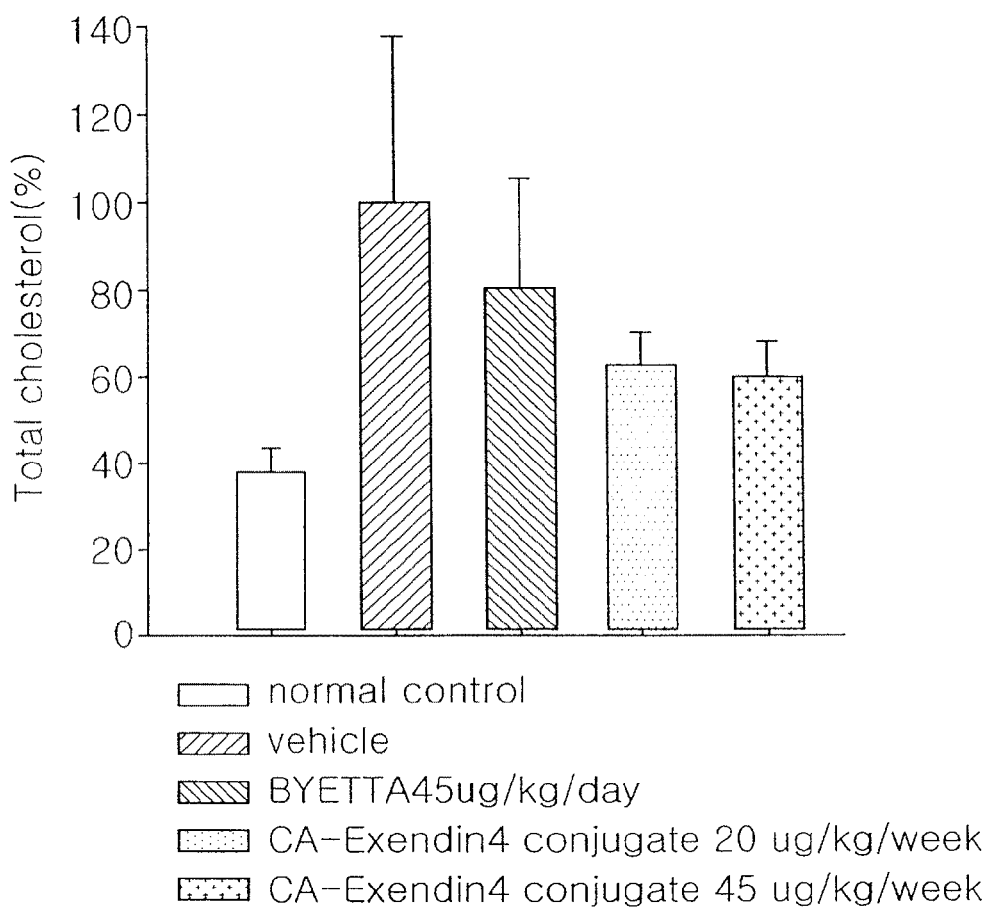

[Fig. 3]
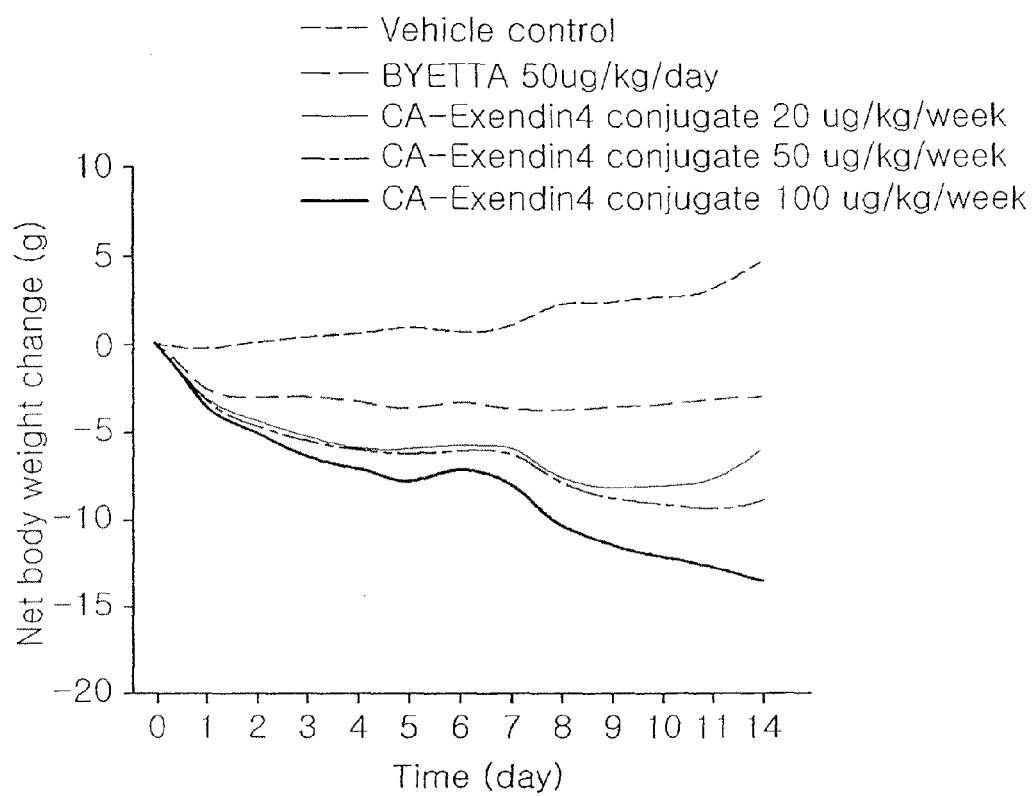

[Fig. 4]
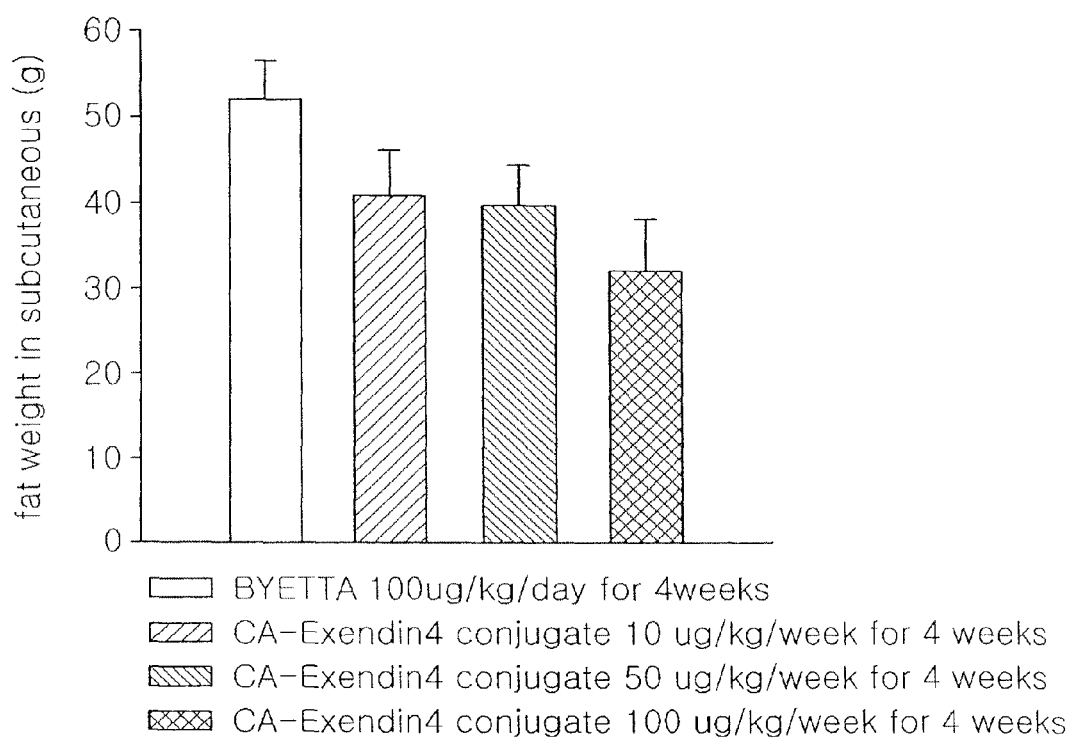

[Fig. 5]
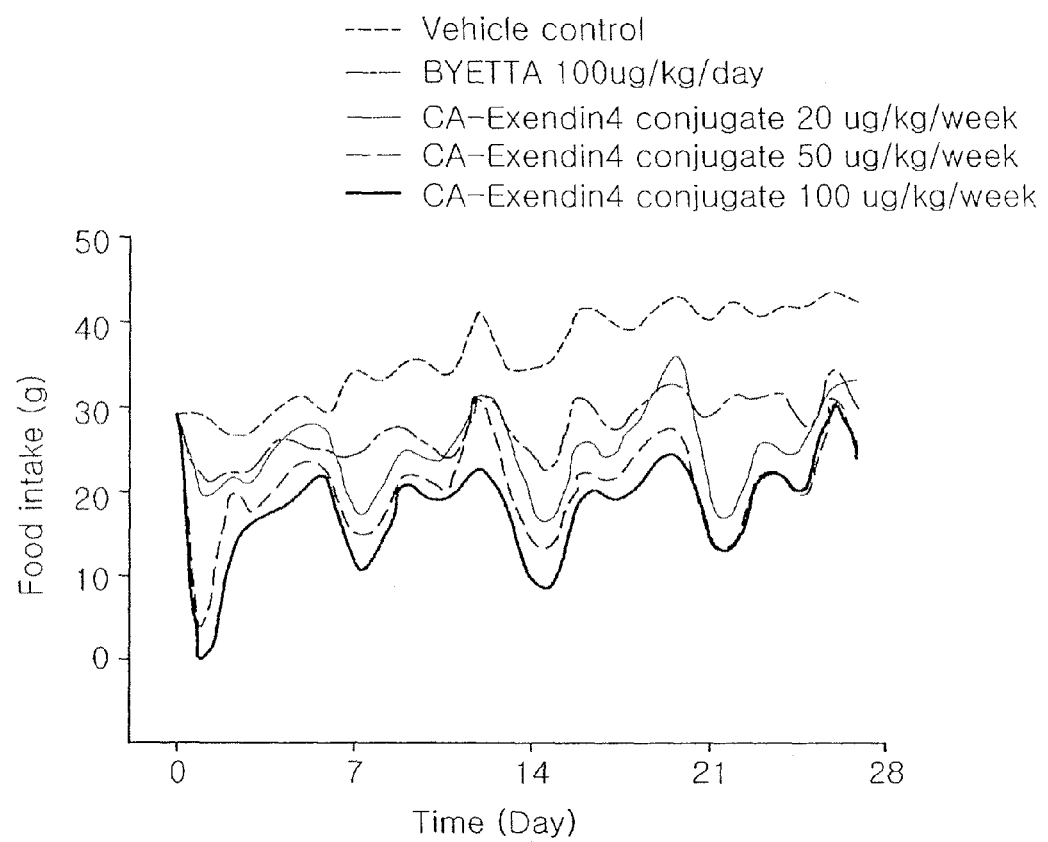

PHARMACEUTICAL COMPOSITION FOR TREATING OBESITY-RELATED DISEASE COMPRISING INSULINOTROPIC PEPTIDE CONJUGATE

CROSS REFERENCE TO RELATED APPLICATIONS

This application is a National Stage of International Application No. PCT/KR2008/007074 filed Nov. 28, 2008, claiming priority based on U.S. patent Ser. No. 11/947,697, filed Nov. 29, 2007 and Korean Patent Application 10-2008-0083194, filed Aug. 26, 2008, the contents of all of which are incorporated herein by reference in their entirety.

TECHNICAL FIELD

The present invention relates to a composition for treating obesity-related diseases comprising an insulinotropic peptide conjugate, more particularly, to a composition for treating obesity-related diseases comprising a conjugate prepared by covalently linking the insulinotropic peptide with a carrier substance via a non-peptidyl linker, and a method for treating obesity-related diseases by using the same.

BACKGROUND ART

Obesity is a chronic disease associated with high morbidity and mortality, caused by adipose tissue accumulation due to disrupted regulation of energy balance or hypernutrition. Obesity and obesity-related diseases are very serious health problems in the United States and all over the world. In the general population of the U.S., over last 7 years, the prevalence of obesity increased from 22.9% to 30.6%. According to the results from the 1999-2002 National Health and Nutrition Examination Survey (NHANES) conducted by U.S. center for Disease Control and Prevention, 29.8% of adults aged 20 years or older were overweight, 30.4% thereof were obese. The prevalence of extreme obesity among adults was 4.9% (Hedley et al., JAMA 2004; 291:2847-50). Obesity is dramatically increasing in not only the U.S. but also in every country that has adopted westernized food and cultural habits. There are currently 250 million obese people in the world, and it is estimated that about 300 million people worldwide will be obese by the year 2025. Obesity itself presents its own health problems, and is also correlated with a variety of other complications such as hypertension, hyperlipidemia, cardiovascular disease and diabetes. About 80% of obese patients have the one or more of the above diseases (Mantzoros et al., J Clin Endocrinol Metab 2000; 85:4000-2), and approximately 300,000 people die each year due to complications from obesity (Allison et al., JAMA 1999; 282:1530-8). A weight gain of just 1 kg has been shown to increase cardiovascular risk by 3.1% and diabetes risk by 4.5-9%, and about 11% weight loss has been shown to reduce the morbidity by 25%. Thus, there is an urgent need to develop therapeutic strategies for obesity (Arbeeny et al., Obes Res 2004; 12:1191-6). In 1893, for the treatment of obesity, thyroid hormone drugs were used to facilitate thermogenesis by noradrenaline and adrenaline. However, these drugs accelerated the loss of lean tissue mass and caused negative nitrogen balance to induce side effects of cardiotoxicity rather than exhibiting the desired effect of reducing adipose tissue. Thus, their use is currently limited to hypothyroidism. In the 1930s, amphetamine was used as an appetite suppressant, but its long term use was prohibited because of drug dependence. Phentermine, diethylpropion, and fenfluramine, which do not induce drug dependence, have been used for the treatment of obesity. However, their use was also prohibited, since most of them caused cardiovascular diseases, hypertension, cardiac dysrhythmia, pulmonary hypertension, and mental disorders such as failing memory. Current therapeutic strategies for obesity include appetite suppressants stimulating central adrenergic receptors or preventing resorption of serotonin, thermogenic beta 3-adrenergic agonists, digestive lipase inhibitors, and hormone regulators such as leptin and PYY (Dunstan et al., Nature reviews drug discovery 2006; 5:919-931). Among them, lipase inhibitors, orlistat and sibutramine, which prevents resorption of serotonin to suppress appetite, are the only FDA-approved drugs, but lead to side effects including steatorrhea, headache, and increased blood pressure. Thus, there are still many difficulties to develop drugs having both safety and efficacy.

GLP-1, a hormone that is secreted by the small intestine, generally promotes the biosynthesis and secretion of insulin, and inhibits the secretion of glucagon to regulate the glucose concentration in blood. It is reported that GLP-1 has the effects of suppressing food intake and reducing body weight upon administration to mice (Meeran et al, Endorinology 1999; 140:244-50), and these effects were shown in both normal and obese mice, indicating its potential as an anti-obesity agent. However, GLP-1 is rapidly degraded by the dipeptidyl peptidase IV (DPPIV), and thus its potential as a drug is very limited. On the other hand, exendin is a peptide that is found in the venom of Gila-monster common in Arizona and Mexico. It has similar physiological activity to GLP-1, but resistance to DPP IV, showing its possibility as a therapeutic agent for diabetes and obesity. Exendin is commercialized as a therapeutic agent for diabetes, which is injected twice a day. In U.S. Pat. No. 6,956,026, U.S. Pat. No. 6,989,366 and U.S. Pat. No. 7,115,569, disclosed is a method for suppressing food intake using exendin and derivatives thereof, in which the efficacy of suppressing food intake is demonstrated, but the effect maintains for 6 hrs after maximum administration. For the treatment of chronic diseases such as obesity, it needs to be injected into a patient several times a day, which is still difficult for patients. In addition, the exendin derivatives described in the patents exhibit differing efficacy, dose-dependency, and duration to each other, and do not show superior efficacy in suppressing food intake to that of native exendin.

DISCLOSURE

Technical Problem

Thus, the present inventors used a preparation method, in which an immunoglobulin Fc region, a non-peptidyl linker, and an insulinotropic peptide are covalently linked to each other as a method for maximizing the effects of increasing the blood half-life of insulinotropic peptide, and of maintaining the in-vivo activity. They have found that the conjugate, in particular, exendin-4, des-amino-histidyl-exendin-4 with removal of the N-terminal amine group, beta-hydroxy-imidazo-propionyl-exendin-4 prepared by substitution of the N-terminal amine group with a hydroxyl group, dimethyl-histidyl-exendin-4 prepared by modification of the N-terminal amine group with two methyl groups, and imidazo-acetyl-exendin-4 with the removal of the alpha carbon of the first amino acid histidine, has a remarkably increased effect of suppressing food intake and in-vivo duration of efficacy, thereby completing the present invention.

Technical Solution

It is an object of the present invention to provide a composition for treating obesity-related diseases, suppressing food intake, and reducing body fat, comprising a conjugate that is prepared by covalently linking an insulinotropic peptide with a carrier substance via a non-peptidyl linker.

It is another object of the present invention to provide a method for treating obesity-related diseases, suppressing food intake, and reducing body fat by using the composition comprising the conjugate.

Advantageous Effects

The composition comprising the insulinotropic peptide conjugate provided by the present invention exhibits the effects of suppressing food intake to reduce body fat and treating obesity-related diseases that are superior to the native insulinotropic peptide. Therefore, the composition is useful for maximizing the therapeutic effect on obesity-related diseases.

DESCRIPTION OF DRAWINGS

FIG. 1 is a graph showing the efficacy for reducing body weight in ob/ob mice;

FIG. 2 is a graph showing changes in body fat in ob/ob mice;

FIG. 3 is a graph showing the efficacy for reducing body weight in DIO animal models;

FIG. 4 is a graph showing the efficacy for reducing body fat in ZDF rats; and

FIG. 5 is a graph showing the efficacy for reducing food intake in ZDF rats.

BEST MODE

In accordance with an aspect, the present invention pertains to a composition for treating obesity-related diseases, suppressing food intake, or reducing body fat, comprising a conjugate that is prepared by covalently linking an insulinotropic peptide with a carrier substance via a non-peptidyl linker.

As used herein, the term "obesity-related diseases" may be selected from the group consisting of overeating, binge eating, and bulimia, hypertension, diabetes, elevated plasma insulin concentrations, insulin resistance, hyperlipidemia, metabolic syndrome, insulin resistance syndrome, obesity-related gastroesophageal reflux, arteriosclerosis, hypercholesterolemia, hyperuricaemia, lower back pain, cardiac hypertrophy and left ventricular hypertrophy, lipodystrophy, nonalcoholic steatohepatitis, cardiovascular diseases, and polycystic ovary syndrome, and the subjects with these obesity-related diseases including those with a desire to lose weight.

As used herein, the term "insulinotropic peptide" is a peptide possessing an insulinotropic function for promoting the synthesis and the expression of insulin in a pancreatic beta cell. These peptides include a precursor, an agonist, a derivative, a fragment, and a variant, and preferably GLP (glucagon like peptide)-1, exendin 3, and exendin 4 or derivatives thereof. The insulinotropic peptide derivative of the present invention is a derivative having a chemically modified N-terminal histidine residue, or a derivative having a chemically modified amino group of N-terminal histidine residue. In addition, the derivative of exendin-4 or exendin-3 refers to a peptide prepared by substitution, deletion or insertion of one or more amino acids into or from the native peptide or a chemically modified peptide, prepared by alkylation, acylation, esterification, or amidation of one or more amino acids in the native peptide, and refers to a peptide having native activity. Examples of the exendin-3 or exendin-4 derivative include, but are not limited to, exendin analogs having partially deleted C-terminus or substitution with non-natural amino acid Norleucine, which is disclosed in WO97/46584, exendin analogs having substitution of non-natural amino acids such as pentylglycine, homoproline, and tertbutylglycine, which is disclosed in WO99/07404, and exendin analogs having a shorter amino acid sequence than that of native exendin by partial deletion of C-terminal amino acid residue, and exendin analogs having substitution with other amino acids, which are disclosed in US 2008/0119390, the disclosure of which is incorporated herein by reference in its entirety. More preferably, the insulinotropic peptide is exendin-4 or derivatives thereof.

In particular, the insulinotropic peptide derivative of the present invention may include a derivative thereof with removal of the N-terminal amino group (Desamino-histidyl-derivative), a derivative thereof prepared by substitution of the amino group with a hydroxyl group (beta-hydroxy imidazopropionyl-derivative), a derivative thereof prepared by modification of the amino group with two methyl residues (Dimethyl-histidyl-derivative), a derivative thereof prepared by substitution of the N-terminal amino group with a carboxyl group (beta-carboxylimidazopropionyl-derivative), or a derivative thereof with removal of the positive charge of the amino group, in which the alpha carbon of N-terminal histidine residue is removed to leave remaining only the imidazoacetyl group, and other N-terminal amino group modified-derivatives.

In the present invention, the insulinotropic peptide derivative is more preferably an exendin 4 derivative having chemically modified N-terminal amino group and amino acid residue, even more preferably an exendin-4 derivative which is prepared by removing or substituting the alpha amino group present in the alpha carbon of N-terminal His[1] residue of exendin-4 or by removing or substituting the alpha carbon. Still even more preferably, as shown in the following <a> to <e>, desamino-histidyl-exendin-4 (DA-Exendin-4) with removal of the N-terminal amino group, beta-hydroxy imidazopropyl-exendin-4 (HY-exendin-4) prepared by substitution of the amino group with a hydroxyl group, beta-carboxy imidazopropyl-exendin-4 (CX-exendin-4) prepared by substitution of the amino group with a carboxyl group, dimethyl-histidyl-exendin-4 (DM-exendin-4) prepared by modification of the amino group with two methyl residues, or imidazoacetyl-exendin-4 (CA-exendin-4) with removal of alpha carbon of N-terminal histidine residue.

<a>

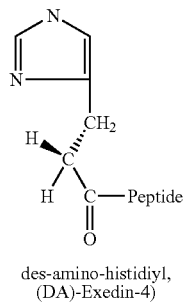

des-amino-histidyl,
(DA)-Exedin-4)

-continued

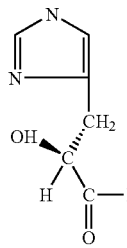

beta-hydroxy-
imidazopropionyl(HY)-Exendin-4)

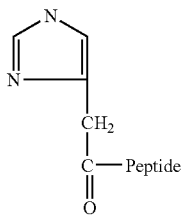

(imidazoacetyl(CA)-Exendin-4)

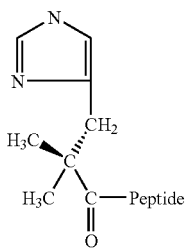

(dimethiyl-histidyl(DM)-Exendin-4)

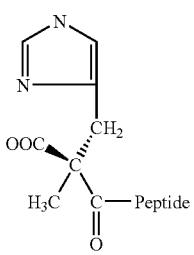

beta-carboxy-
imidazopropionyl(CX)-Exendin-4)

The carrier substance which can be used in the present invention is a substance which is covalently linked to the insulinotropic peptide via the non-peptidyl linker, and remarkably increases the blood half-life of the peptide, and can be selected from the group consisting of an immunoglobulin Fc region, serum albumin, transferrin, collagen and fragments thereof, fibronectin and fragments thereof, and PEG, and preferably an immunoglobulin Fc region. The term "immunoglobulin Fc region" as used herein, refers to a protein that contains the heavy-chain constant region 2 ($C_H2$) and the heavy-chain constant region 3 ($C_H3$) of an immunoglobulin, excluding the variable regions of the heavy and light chains, the heavy-chain constant region 1 ($C_H1$) and the light-chain constant region 1 ($C_L1$) of the immunoglobulin. It may further include a hinge region at the heavy-chain constant region. Also, the immunoglobulin Fc region of the present invention may contain a part or all of the Fc region including the heavy-chain constant region 1 ($C_H1$) and/or the light-chain constant region 1 ($C_L1$), except for the variable regions of the heavy and light chains, as long as it has a physiological function substantially similar to or better than the native protein. Also, the immunoglobulin Fc region may be a fragment having a deletion in a relatively long portion of the amino acid sequence of $C_H2$ and/or $C_H3$. That is, the immunoglobulin Fc region of the present invention may comprise 1) a $C_H1$ domain, a $C_H2$ domain, a $C_H3$ domain and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of one or more domains and an immunoglobulin hinge region (or a portion of the hinge region), and 6) a dimer of each domain of the heavy-chain constant regions and the light-chain constant region. The immunoglobulin Fc region of the present invention includes a native amino acid sequence, and a sequence derivative (mutant) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in WO 97/34631 and WO 96/32478. Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc region, if desired, may be modified by phosphorylation, sulfation, acrylation, glycosylation, methylation, farnesylation, acetylation, amidation, and the like. The aforementioned Fc derivatives are derivatives that have a biological activity identical to the Fc region of the present invention or improved structural stability, for example, against heat, pH, or the like. In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)$_2$ fragments. These fragments may be subjected, for example, to size exclusion chromatography to isolate Fc or pF'c. Preferably, a human-derived Fc region is a recombinant immunoglobulin Fc region that is obtained from a microorganism. In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier. As used herein, the term "deglycosylation" refers to enzymatically removing sugar moieties from an Fc region, and the term "aglycosylation" means that an Fc region is produced in an unglycosylated form by a prokaryote, preferably E. coli. On the other hand, the immunoglobulin Fc region may be derived from humans or other animals including cows, goats, swine, mice, rabbits, hamsters, rats and guinea pigs, and preferably humans. In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of ligand-binding proteins. On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments. The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of $C_H1$, $C_H2$, $C_H3$ and $C_H4$ of IgG Fc, IgM Fc, IgA Fc, IgE Fc and IgD Fc, and may include the hinge region. On the other hand, IgG is divided into IgG1, IgG2, IgG3 and IgG4 subclasses, and the present invention includes combinations and hybrids thereof. Preferred are IgG2 and IgG4 subclasses, and most preferred is the Fc region of IgG4 rarely having effector functions such as CDC (complement dependent cytotoxicity). That is, as the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

In the conjugate contained in the composition of the present invention, the insulinotropic peptide is linked to the carrier substance via a non-peptidyl linker. The term "non-peptidyl linker", as used herein, refers to a singe compound or a biocompatible polymer including two or more repeating units linked to each other. The non-peptidyl linker which can be used in the present invention may have any chemical structure, and primarily functions as a linker linking the insulinotropic peptide and the carrier substance to each other by a covalent bond. Thus, the non-peptidyl linker is characterized in that it is a chemical compound having reactive groups capable of covalently binding to peptide/carrier substance at both ends, in which the terminal reactive group at both ends are the same as or different from each other. The reactive groups at both ends of the non-peptidyl linker may be the same or different. For example, the non-peptidyl linker may have a maleimide group at one end and an aldehyde group, a propionic aldehyde group, or a butyl aldehyde group at the other end. The reactive groups at both ends of the non-peptidyl linker are preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl linker has a reactive aldehyde group at both ends, it is effective in linking at both ends with a physiologically active polypeptide and an immunoglobulin Fc region with minimal non-specific reactions. A final product generated by reductive alkylation by an aldehyde bond is much more stable than when linked by an amide bond. The aldehyde reactive group selectively binds to N-terminus at a low pH, and can bind to a lysine residue to form a covalent bond at a high pH, such as pH 9.0. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the insulinotropic peptide conjugate of the present invention. The non-peptidyl polymer which can be used in the present invention may be SMCC (succinimidyl 4-(N-maleimido-methyl) cyclohexane-1-carboxylate), or SFB (succinimidyl 4-formyl-benzoate) which can be covalently linked to the amine and sulfhydryl groups of the peptide, but is not limited thereto. The non-peptidyl polymer may be selected from the group consisting of polyethylene glycol, polypropylene glycol, polyvinylpyrrolidone, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid) and PLGA (polylactic-glycolic acid), lipid polymers, chitins, hyaluronic acid, and combinations thereof, and preferred is polyethylene glycol. Also, derivatives thereof well known in the art and being easily prepared within the skill of the art are included in the scope of the present invention.

Preferred examples of the conjugate, which is contained in the composition for treating obesity-related diseases according to the present invention, prepared by covalently linking the insulinotropic peptide with a carrier substance via a non-peptidyl linker, are disclosed in WO08/082,274, and represented by the following Formula 1.

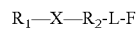  <Formula 1>

$R_1$—X—$R_2$-L-F wherein $R_1$ is selected from the group consisting of des-amino-histidyl, dimethyl-histidyl, beta-hydroxy imidazopropionyl, 4-imidazoacetyl and beta-carboxy imidazopropionyl,
$R_2$ is selected from the group consisting of —$NH_2$, —OH and -Lys,
X is selected from the group consisting of
Gly-Glu-Gly-Thr-Phe-Thr-Ser-Asp-Leu-Ser-Y-Gln-Met-Glu-Glu-Glu-Ala-Val-Arg-Leu-Phe-Ile-Glu-Trp-Leu-Z-Asn-Gly-Gly-Pro-Ser-Ser-Gly-Ala-Pro-Pro-Pro-Ser, Gly-Glu-Gly-Thr-Phe-Thr-Ser-Asp-Leu-Ser-Y-Gln-Met-Glu-Glu-Glu-Ala-Val-Arg-Leu-Phe-Ile-Glu-Trp-Leu-Z-Asn-Gly-Gly and
Ser-Asp-Gly-Thr-Phe-Thr-Ser-Asp-Leu-Ser-Y-Gln-Met-Glu-Glu-Glu-Ala-Val-Arg-Leu-Phe-Ile-Glu-Trp-Leu-Z-Asn-Gly-Gly-Pro-Ser-Ser-Gly-Ala-Pro-Pro-Pro-Ser,
Y is selected from the group consisting of Lys, Ser and Arg,
Z is selected from the group consisting of Lys, Ser and Arg
L is a non-peptidyl linker, and
F is an immunoglobulin Fc.

In addition, the pharmaceutical composition comprising the conjugate of the present invention may comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampule as a single-dose dosage form. The pharmaceutical composition may be also formulated into solutions, suspensions, tablets, pills, capsules and long-acting preparations. On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, perfumes, and antiseptics. The administration dose of the pharmaceutical composition of the present invention can be determined by several related factors including the types of diseases to be treated, administration routes, the patient's age, gender, weight and severity of the illness. Since the pharmaceutical composition of the present invention has excellent duration of in-vivo efficacy and titer, it can remarkably reduce the administration frequency and dose of pharmaceutical drugs comprising the composition of the present invention.

The insulinotropic peptide conjugate contained in the composition of the present invention exhibits the sustained effect of suppressing food intake in a much smaller amount than the native insulinotropic peptide, thereby being used for the treatment of diseases such as obesity and acute coronary syndrome. In addition, owing to the effect of suppressing food intake (appetite suppression), the insulinotropic peptide conjugate can be used for reducing body fat such as cholesterol and adipose tissue. For the treatment of obesity and obesity-related diseases, the reduction in body fat is needed, but the loss of lean tissue, that is, protein loss, is not preferable. Since the lean body mass consists of muscles, vital organs, bone, connective tissue and other non-fat tissues, loss of the lean body mass is believed to be harmful to human health. Accordingly, weight loss due to appetite suppression by the composition according to the present invention leads to the reduction not in lean body mass but in adipose tissue, and thus functions as a very important factor for the treatment of obesity-related diseases.

Since the insulinotropic peptides such as GLP-1, amylin, CCK and exendin maintain their efficacy for suppressing appetite at a short duration of 1 to 6 hrs after administration, they have to be repeatedly administered for the treatment of chronic diseases such as obesity and obesity-related diseases. The insulinotropic peptide conjugate contained in the composition of the present invention maintains its efficacy at a low dose over one week, thereby exhibiting the maximum therapeutic efficacy.

In accordance with still another aspect, the present invention relates to a method for treating obesity-related diseases, a method for suppressing food intake, and a method for reducing body fat by using the composition. In particular, the method according to the present invention may comprise the step of administering a therapeutically acceptable amount of the composition.

The term "administration", as used herein, means introduction of a predetermined amount of a substance into a patient by a certain suitable method. The composition comprising the conjugate may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell. In this regard, a therapeutically acceptable dose of the composition may be determined depending on the aforementioned various factors.

In accordance with still another aspect of the present invention, the present invention provides a pharmaceutical composition for the treatment of obesity-related diseases using the insulinotropic peptide conjugate alone or in combination with one or more anti-obesity drugs. Examples of the substances constituting the pharmaceutical composition for the treatment of obesity-related diseases in combination with the insulinotropic peptide conjugate include substances showing appetite-suppressing or energy metabolism-boosting activity, lipid degradation-suppressing activity, retardation activity of gastric emptying, protein tyrosine phosphatase (PTP) 1b-inhibiting activity and DPPIV-inhibiting activity, such as GLP-1 and derivatives thereof (Patricia., Trends in endocrinology and metabolism 2007; 18:240-245), amylin, PYY (peptideYY) (Lynn et al., Bioorganic & Medicinal Chemistry Letters 2007; 17:1916-1919), leptin, cholecytokinin (CCK), oxyntomodulin, ghrelin antagonist, NPY antagonist (Elena et al., Nutrition, Metabolism & Cardiovascular Disease 2008; 18:158-168), Sarika et al., Neuropeptides 2006; 40:375-401), rimonabant, sibutramine, and orlistat (Alan Dove., Nature biotechnology 2001; 19:25-28), but are not limited thereto.

MODE FOR INVENTION

Hereinafter, a better understanding of the present invention may be obtained through the following examples which are set forth to illustrate, but are not to be construed as the limit of the present invention.

Example 1

Preparation of Insulinotropic Peptide Conjugate (CA-Exendin)

3.4K PropionALD(2) PEG (PEG having two propionaldehyde groups, IDB Inc., Korea) and the lysine residue of imidazo-acetyl Exendin-4 (Bachem, Swiss) were subjected to pegylation by reacting the peptide and the PEG at 4° C. overnight at a molar ratio of 1:15, with a peptide concentration of 5 mg/ml. At this time, the reaction was performed in a buffering agent at pH 7.5, and 20 mM SCB(NaCNBH$_3$) as a reducing agent was added thereto to perform the reaction. A mono-pegylated exendin and isomers were isolated using SOURCE S (XK 16 ml, Amersham Biosciences) under the following conditions.
Column: SOURCE S (XK 16 ml, Amersham Biosciences)
Flow rate: 2.0 ml/min
Gradient: A 0→100% 45 min B (A: 20 mM citric acid pH 3.0, B: A+0.5 M KCl)

The isolated mono pegylated CA-Exendin-4 was coupled with immunoglobulin Fc. The reaction was performed at a ratio of peptide:immunoglobulin Fc of 1:4, and a total concentration of proteins of 50 mg/ml at 4° C. for 16 hours. The reaction was performed in a solution of 100 mM K-P (pH 6.0), and 20 mM SCB as a reducing agent was added thereto. After the coupling reaction, two purification steps were performed using SOURCE Phe (16 ml) and SOURCE Q (16 ml).
Column: SOURCE Phe (HR16 ml, Amersham Biosciences)
Flow rate: 2.0 mL/min
Gradient: B 100→0% 30 min B (A: 20 mM Tris pH7.5, B: A+1.5 M NaCl)
Column: SOURCE Q (XK16 ml, Amersham Biosciences)
Flow rate: 2.0 ml/min
Gradient: A 0→25% 60 min B (A: 20 mM Tris pH7.5, B: A+1 M NaCl)

Example 2

Weight Loss Effect of Insulinotropic Peptide Conjugate in ob/ob Mouse

A well-known animal model for obesity, ob/ob mice (C57BL/6JHamSlc-ob/bo, female, 8-9 week old) were divided into 4 groups (5 mice each group), and then administered with vehicle and Byetta (Amylin-Lily, exendin-4, 45 μg/kg, subcutaneous injection everyday) and the insulinotropic peptide conjugate prepared in Example 1 (45 μg or 100 μg/kg, subcutaneous injection once a week). Then, changes in body weight were measured for 28 days, and blood levels of parameters of lipid metabolism, such as cholesterol and free fatty acid, were measured after completion of the administration. After completion of the test, the livers and adipose tissues were dissected out, and weighed. The weight loss effects of the insulinotropic peptide conjugate in ob/ob mouse are shown in Table 1.

TABLE 1

| Test Materials | Vehicle | Byetta (Exendin-4) | Insulinotropic peptide conjugate | |
|---|---|---|---|---|
| Dosage (μg/kg) | — | 45 | 45 | 100 |
| Total dose (μg/kg) | — | 1260 | 180 | 400 |
| Injection interval (for 4 weeks) | — | day | week | week |
| Body weight (%) | 100 | 87.1 | 72.1 | 62.2 |
| Total cholesterol (%) | 100 | 80.3 | 62.4 | 59.7 |
| Adipocyte index (%) | 100 | 96.4 | 88.9 | 81.2 |

As shown in Table 1 and FIGS. 1 and 2, the insulinotropic peptide conjugate showed the effects of reducing body weight and cholesterol level superior to Byetta at a dose of 1/7, and the effects were dose-dependent. In addition, the efficacy in administration of the insulinotropic peptide conjugate once a week maintained longer than that in the everyday administration of exendin-4.

Example 3

Weight Loss Effect of Insulinotropic Peptide Conjugate in DIO Mouse

A well-known animal model for obesity, DIO (diet induced obesity) mice (C57BL/6NCrjBgi, male, 25 week old) were divided into 5 groups (5 mice each group), and then administered with vehicle and Byetta (100 μg/kg, subcutaneous injection everyday) and the insulinotropic peptide conjugate prepared in Example 1 (20, 50, 100 μg/kg, subcutaneous injection once a week). Then, changes in body weight were measured for 2 weeks. The weight loss effects of the insulinotropic peptide conjugate in DIO mouse are shown in Table 2.

TABLE 2

| Test Materials | Vehicle | Byetta | Insulinotropic peptide conjugate | | |
|---|---|---|---|---|---|
| Dosage (μg/kg) | — | 50 | 20 | 50 | 100 |
| Total dose (μg/kg) | — | 700 | 40 | 100 | 200 |
| Injection interval (for 2 weeks) | — | Day | week | week | Week |
| Body weight loss ratio (%) vs. vehicle | 0 | 6.2 | 13.4 | 19.1 | 29.0 |

As shown in Table 2 and FIG. 3, the insulinotropic peptide conjugate showed the effects of reducing body weight superior to Byetta at a dose of 1/17.5, and the effects were dose-dependent. In addition, the efficacy in administration of the insulinotropic peptide conjugate once a week maintained longer than that in the everyday administration of exendin-4.

Example 4

Weight Loss Effect of Insulinotropic Peptide Conjugate in ZDF (Zucker Diabetic Fat) Rat ZDF rats that are generally used in diabetes test studies and have similar features to ob/ob mice (ZDF/Gmi-fa/fa, male, 7 week old) were divided into 5 groups (5 mice each group), and then administered with vehicle and Byetta (100 μg/kg, subcutaneous injection everyday) and the insulinotropic peptide conjugate prepared in Example 1 (20, 50, 100 μg/kg, subcutaneous injection once a week). Then, changes in body weight and feed intake were measured for 8 weeks, and blood levels of parameters of lipid metabolism, such as cholesterol, were measured after completion of the administration. After completion of the test, the adipose tissues were dissected out, and weighed. The weight loss effects of the insulinotropic peptide conjugate in ZDF rat are shown in Table 3.

TABLE 3

| Test Materials | Byetta | insulinotropic peptide conjugate | | |
|---|---|---|---|---|
| Dosage (μg/kg) | 100 | 20 | 50 | 100 |
| Total dose (μg/kg) | 2800 | 80 | 200 | 400 |
| Injection interval (4 weeks) | day | week | week | week |
| Body weight (%) | 100 | 91.3 | 87.3 | 84.7 |
| Fat in Subcutaneous (%) | 100 | 78.5 | 76.9 | 61.6 |
| Fat in Adipocyte (%) | 100 | 87.1 | 82.3 | 74.6 |

As shown in Table 3 and FIGS. 4 and 5, the insulinotropic peptide conjugate showed the effects of reducing body weight and body fat and suppressing food intake superior to Byetta at a dose of 1/35, and the effects were dose-dependent. In addition, the efficacy in administration of the insulinotropic peptide conjugate once a week maintained longer than that in the everyday administration of exendin-4.

What is claimed is:

1. A method for treating obesity-related diseases comprising administering to a subject in need thereof a composition, said composition comprising an insulinotropic peptide conjugate, which is prepared by linking an insulinotropic peptide with an immunoglobulin Fc region via a non-peptidyl linker,
   wherein the non-peptidyl linker is selected from the group consisting of succinimidyl 4-(N-maleimido-methyl)cyclohexane-l-carboxylate, succinimidyl 4-formylbenzoate), polyethylene glycol, polypropylene glycol, polyvinylpyrrolidone, copolymers of ethylene glycol and propylene glycol, polyoxyethylated polyols, polyvinyl alcohol, polysaccharides, dextran, polyvinyl ethyl ether, biodegradable polymers such as polylactic acid and polylactic-glycolic acid, lipid polymers, chitins, hyaluronic acid, and combinations thereof; and
   wherein the insulinotropic peptide is imidazo-acetyl exendin-4 where the alpha carbon of the N-terminal histidine residue is deleted.

2. The method for treating obesity-related diseases according to claim 1, wherein the obesity-related disease is selected from the group consisting of obesity, hyperlipidemia, insulin resistance syndrome, obesity-related gastroesophageal reflux, steatohepatitis, cardiovascular diseases, and metabolic syndrome.

3. The method for treating obesity-related diseases using the composition according to claim 1, wherein the composition further comprises one selected from the group consisting of glucagon like peptide-1 and variants thereof, amylin, peptide YY, leptin, cholecytokinin, oxyntomodulin, ghrelin antagonists, neuropeptide antagonists, rimonabant, sibutramine, and orlistat.

4. The method for treating obesity-related diseases according to claim 1, wherein the non-peptidyl linker is polyethylene glycol.

5. A method for suppressing food intake comprising administering to a subject in need thereof a composition, said composition comprising an insulinotropic peptide conjugate, which is prepared by linking an insulinotropic peptide with an immunoglobulin Fc region via a non-peptidyl linker,
   wherein the non-peptidyl linker is selected from the group consisting of succinimidyl 4-(N-maleimido-methyl)cyclohexane-l-carboxylate, succinimidyl 4-formylbenzoate, polyethylene glycol, polypropylene glycol, polyvinylpyrrolidone, copolymers of ethylene glycol and propylene glycol, polyoxyethylated polyols, polyvinyl alcohol, polysaccharides, dextran, polyvinyl ethyl ether, biodegradable polymers such as polylactic acid and polylactic-glycolic acid, lipid polymers, chitins, hyaluronic acid, and combinations thereof; and
   wherein the insulinotropic peptide is imidazo-acetyl exendin-4 where the alpha carbon of the N-terminal histidine residue is deleted.

6. A method for reducing body fat or plasma cholesterol comprising administering to a subject in need thereof a composition, wherein the composition comprising an insulinotropic peptide conjugate, which is prepared by linking an insulinotropic peptide with an immunoglobulin Fc region via a non-peptidyl linker,
   wherein the non-peptidyl linker is selected from the group consisting of succinimidyl 4-(N-maleimido-methyl)cyclohexane-l-carboxylate, succinimidyl 4-formylbenzoate, polyethylene glycol, polypropylene glycol, polyvinylpyrrolidone, copolymers of ethylene glycol and propylene glycol, polyoxyethylated polyols, polyvinyl alcohol, polysaccharides, dextran, polyvinyl ethyl ether, biodegradable polymers such as polylactic acid and polylactic-glycolic acid, lipid polymers, chitins, hyaluronic acid, and combinations thereof; and
   wherein the insulinotropic peptide is imidazo-acetyl exendin-4 where the alpha carbon of the N-terminal histidine residue is deleted.

* * * * *

SEQUENCE LISTING

<160> NUMBER OF SEQ ID NOS: 3

<210> SEQ ID NO 1
<211> LENGTH: 38
<212> TYPE: PRT
<213> ORGANISM: Artificial Sequence
<220> FEATURE:
<223> OTHER INFORMATION: Synthetic construct (A part X of insulinotropic
      peptide conjugate (Formula 1))
<220> FEATURE:
<221> NAME/KEY: PEPTIDE
<222> LOCATION: (1)..(38)
<223> OTHER INFORMATION: Xaa in amino acid position 11 and Xaa in amino
      acid position 26, which may be identical or different, are each
      independently Lys, Ser or Arg.

<400> SEQUENCE: 1

Gly Glu Gly Thr Phe Thr Ser Asp Leu Ser Xaa Gln Met Glu Glu Glu
 1               5                  10                  15

Ala Val Arg Leu Phe Ile Glu Trp Leu Xaa Asn Gly Gly Pro Ser Ser
            20                  25                  30

Gly Ala Pro Pro Pro Ser
        35

<210> SEQ ID NO 2
<211> LENGTH: 29
<212> TYPE: PRT
<213> ORGANISM: Artificial Sequence
<220> FEATURE:
<223> OTHER INFORMATION: Synthetic construct (A part X of insulinotropic
      peptide conjugate (Formula 1))
<220> FEATURE:
<221> NAME/KEY: PEPTIDE
<222> LOCATION: (1)..(29)
<223> OTHER INFORMATION: Xaa in amino acid position 11 and Xaa in amino
      acid position 26, which may be identical or different, are each
      independently Lys, Ser or Arg.

<400> SEQUENCE: 2

Gly Glu Gly Thr Phe Thr Ser Asp Leu Ser Xaa Gln Met Glu Glu Glu
 1               5                  10                  15

Ala Val Arg Leu Phe Ile Glu Trp Leu Xaa Asn Gly Gly
            20                  25

<210> SEQ ID NO 3
<211> LENGTH: 38
<212> TYPE: PRT
<213> ORGANISM: Artificial Sequence
<220> FEATURE:
<223> OTHER INFORMATION: Synthetic construct (A part X of insulinotropic
      peptide conjugate (Formula 1))
<220> FEATURE:
<221> NAME/KEY: PEPTIDE
<222> LOCATION: (1)..(38)
<223> OTHER INFORMATION: Xaa in amino acid position 11 and Xaa in amino
      acid position 26, which may be identical or different, are each
      independently Lys, Ser or Arg.

<400> SEQUENCE: 3

Ser Asp Gly Thr Phe Thr Ser Asp Leu Ser Xaa Gln Met Glu Glu Glu
 1               5                  10                  15

Ala Val Arg Leu Phe Ile Glu Trp Leu Xaa Asn Gly Gly Pro Ser Ser
            20                  25                  30

Gly Ala Pro Pro Pro Ser
        35